May 12, 1953 O. L. WEEKS Plant Pat. 1,185
ROSE PLANT
Filed Feb. 1, 1952
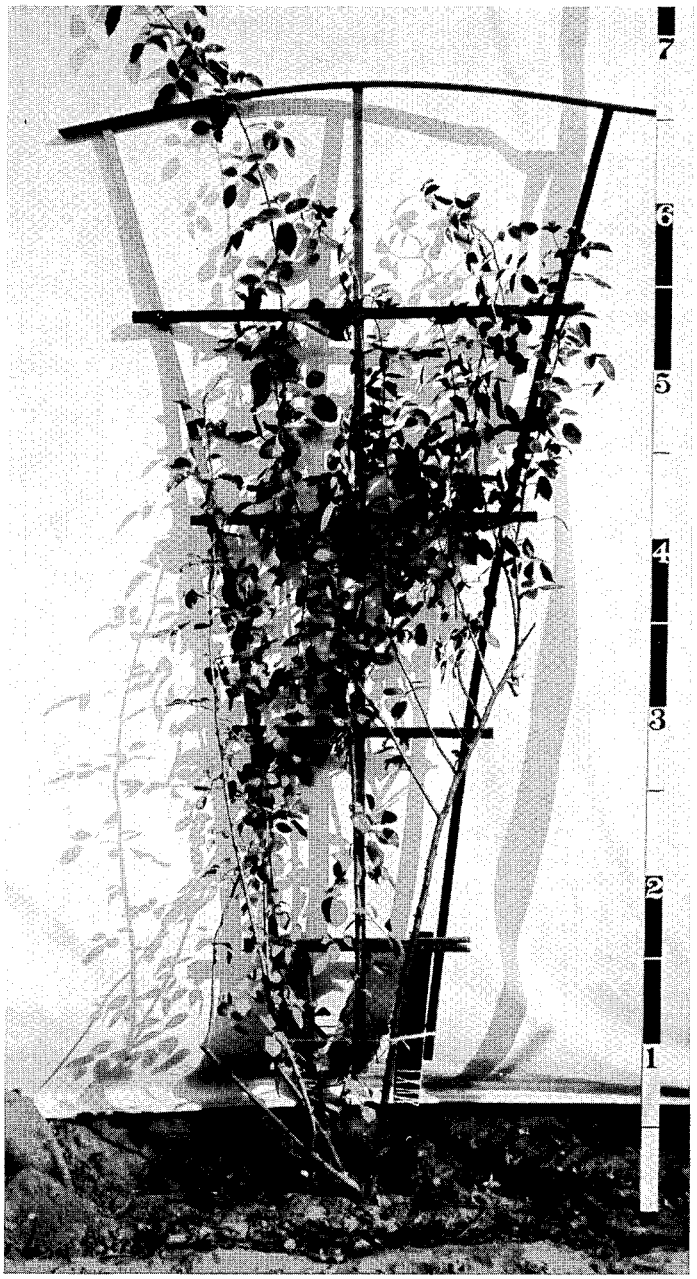
Inventor.
O. L. Weeks
By Robert Cobb
Attorneys.

Patented May 12, 1953

Plant Pat. 1,185

UNITED STATES PATENT OFFICE 1,185

ROSE PLANT

O. L. Weeks, Chino, Calif., assignor to Armstrong Nurseries, Inc., Ontario, Calif., a corporation of California Application February 1, 1952, Serial No. 269,389

1 Claim. (Cl. 47—61)

The present invention relates to a new and distinct variety of rose plant of the climbing hybrid tea class, originating as a cultivated sport of the variety "Sutter's Gold" (Plant Patent No. 885), and dominantly distinguished therefrom by its vigorous growing habit as characterized by its strong climbing canes attaining a mature height of from 10 to 14 feet or more, as distinguished from the usual height of 4 to 6 feet attained by the bush parent; by its habit of producing many more flowers in the spring than can be found at any one time on the parent variety; and by its intermittent flowering habit during the remainder of the growing season.

The new variety was discovered by me in a cultivated nursery row of "Sutter's Gold" plants growing in fields under my control at Chino, California.

The parent variety "Sutter's Gold" is a bush rose of the hybrid tea class, and is primarily notable for its production of large, leathery and glossy foliage, its high degree of resistance to mildew and blackspot, the attractive coloring and form of its buds and flowers in their various stages of development, the long, strong flower stems and their relative freedom from prickles, and by the penetrating tea-rose fragrance of its flowers. However, this bush parent, so far as I am aware, has never exhibited a climbing habit, and its growth has been that of the average strong bush rose that usually attains a height of only 4 to 6 feet.

The new variety is generally similar to its parent, except for the dominant distinguishing characteristics noted at the commencement hereof, as more particularly evidenced by the climbing habit of growth of the new variety.

Asexual reproduction of the new variety by budding at Ontario, California, shows that the foregoing characteristics and distinctions come true to form and are established and transmitted through succeeding propagations.

The accompanying drawing shows a specimen plant of the new variety in association with a foot-marked scale at one side of the plant, and illustrates the typical climbing habit of growth of the new variety.

In view of the similarities in general characteristics between the new variety and its parent, excepting for the dominant distinguishing characteristics noted in the foregoing, it is unnecessary to describe the new variety in detail since it substantially conforms to the detailed description contained in the above-noted patent, to which reference may be readily had.

I claim:

A new and distinct variety of rose plant of the climbing hybrid tea class, substantially as herein shown and described, characterized as to novelty particularly by its general similarity to its parent "Sutter's Gold" (Plant Patent No. 885), but essentially distinguished therefrom by its vigorous growing habit as characterized by its strong, climbing canes, by its habit of producing many more flowers in the spring than can be found at any one time on plants of its parent variety, and by its intermittent flowering habit during the remainder of the growing season.

O. L. WEEKS.

No references cited.